United States Patent [19]

Sirkar et al.

[11] Patent Number: 5,510,257
[45] Date of Patent: Apr. 23, 1996

[54] HOLLOW FIBER IMMOBILIZATION WITH CHOPPED MICROPOROUS HOLLOW FIBERS

[76] Inventors: Kamalesh K. Sirkar, 60 Saw Mill Dr., Berkeley Heights, N.J. 07922; Rajesh K. Shukla, 103 Thorn St., Jersey City, N.J. 07307

[21] Appl. No.: 417,981

[22] Filed: Oct. 4, 1989

[51] Int. Cl.$^6$ .............................. C12N 11/04; C12N 5/00; C12N 1/00; C12N 1/20; C12N 1/14; C12N 1/16; C12M 3/00; C12M 3/04; C12M 1/04

[52] U.S. Cl. ................................. 435/182; 435/240.242; 435/243; 435/252.1; 435/254.1; 435/255.1; 435/240.1; 435/289.1; 435/293.1; 435/297.4; 435/299.1

[58] Field of Search ............................ 435/240.242, 182, 435/240.2, 240.241, 240.4, 240.1, 243, 284, 313, 287, 285, 252.1, 254.1, 255.1

[56] References Cited

U.S. PATENT DOCUMENTS

| | | | |
|---|---|---|---|
| 3,883,393 | 5/1975 | Knazek et al. | 435/240.242 |
| 4,144,126 | 3/1979 | Burbidge | 435/240.24 |
| 4,649,114 | 3/1987 | Miltenburger et al. | 435/240.25 |
| 4,770,852 | 9/1988 | Takahara et al. | 422/48 |
| 5,162,225 | 11/1992 | Sager et al. | 435/240.243 |

OTHER PUBLICATIONS

Thilly; *Mammalian Cell Technology*; Butterworths, Boston London Durban Singapore Sydney Toronto Wellington; 1986; pp. 184–186.

Black, et. al. Practical Reactor Systems for Yeast Cell Immobilization Using Biomass Support Particles Biotechnology & Bioengineering vol. 26 pp. 134–141 1984.

I. Chibata, "*Immobilized Enzymes—Research and Development*", Kodansha, Tokyo, Japan (1978) only to p. 73 provided.

W. L. Chick et al., *Animal Cell Entrapment*, Science, 197: 780 (1979).

D. S. Inloes et al., *Appl. Environ. Microbiol.* 46: 264–278 (1983).

S. F. Karel et al., *Chem. Eng. Sci.*, 40: 1321–1354 (1985).

A. M. Klibanov, *Science*, 219:722 (1983).

J. E. Prenosil et al., *Enzyme Microb. Technol.*, 5: 323 (1983).

M. L. Shuler, Plant Cell Immobilization Ann. N.Y. Acad. Sci., 369: 65 (1981).

K. Venkatasubramanian, *Desalination*, 35: 353 (1980).

Primary Examiner—Marion C. Knode
Assistant Examiner—Susan M. Dadio
Attorney, Agent, or Firm—Pennie & Edmonds

[57] ABSTRACT

Most of the problems of prior art techniques for growing cells in hollow fiber devices can be avoided by growing the cells in short lengths (e.g., two inches (5.0 cm.) or less) of microporous hollow fibers. The fibers are prepared by chopping commercial lengths of hollow fibers into small pieces, preferably two inches (5 cm.) or smaller. Such chopped hollow fibers or bundles of hollow fibers are then added to a suitable medium for growth of cells and the medium is incubated. Very high cell densities have been observed in the chopped fibers.

14 Claims, 9 Drawing Sheets

○   1/4" FIBER : (X-20,400 um I.D.)

●   1/16" FIBER : (X-20,400 um I.D.)

○ 400 um I.D. , 1/16″ (X-20)
● 240 um I.D. , 1/16″ (X-20)
△ 100 um I.D. , 1/16″ (X-10)

HOLLOW FIBER IMMOBILIZATION WITH CHOPPED MICROPOROUS HOLLOW FIBERS

BACKGROUND OF THE INVENTION

The present invention relates to improvements in the use of hollow fibers for immobilization of whole cells and the like.

Several techniques are known in the art for immobilization of whole cells for purposes such as extended fermentation. These include surface attachment, entrapment within porous matrices, self aggregation and containment behind a barrier. See, for example, I. Chibata, "Immobilized Enzymes—Research and Development", Kodansha, Tokyo, Japan (1978); K. Venkatasubramanian, *Desalination*, 35; 353 (1980); A. M. Klibanov, *Science*, 219:722 (1983); S. F. Karel et al., *Chem. Eng. Sci.*, 40: 1321–1354 (1985).

Of particular interest is the use of hollow fiber immobilization systems. Such systems use continuous lengths of hollow fibers whose ends are potted in tube sheets. In such systems, the cells may be entrapped in the fiber lumen with substrate solution flowing on the shell side of the device. Alternatively, the cells are entrapped on the shell side (the extra capillary space) and substrate solution flows generally through the fiber lumen. Higher cell densities, maintenance of cell viability for extended periods, continuous removal of product and inhibitory wastes, isolation of cells from the main substrate stream, and higher volumetric productivities are major advantages for such devices.

Applications include yeast immobilization (D. S. Inloes et al., *Appl. Environ. Microbiol.*, 46: 264 (1983)); plant cell immobilization (M. L. Shuler, *Ann. N.Y. Acad. Sci.*, 369: 65 (1981); J. E. Prenosil et al., *Enzyme Microb. Technol.*, 5: 323 (1983)) and animal cell entrapment (W. L. Chick et al., *Science*, 197: 780 (1979)).

However, presently available hollow fiber devices have several limitations. Hollow fiber walls tend to rupture because of uncontrolled cell growth. There are also limitations on diffusion through the fibers as well as problems relating to membrane leakage, gas supply and removal of products and wastes. See, for example, D. S. Inloes et al., *Appl. Environ. Microbiol.*, 46: 264–278 (1983).

SUMMARY OF THE INVENTION

We have found that most of the problems of prior art techniques for growing cells in hollow fiber devices can be avoided by growing the cells in short lengths (e.g., two inches (5.0 cm.) or less) of microporous hollow fibers. More particularly, we have found that very high cell densities can be achieved if the cells are grown in microporous hydrophobic or hydrophilic hollow fibers or bundles of such fibers. Cell growth occurs both in the fiber lumen and on the outside surface of the fiber. Cell density has been observed to increase both as the length of the fiber decreases and as the diameter of the fiber lumen decreases.

In practicing the invention, the fibers are prepared by chopping commercial lengths of hollow fibers into small pieces, preferably two inches (5 cm.) or smaller. Typical hollow fibers used in the practice of the invention include hydrophobic microporous fibers such as Celgard X-20 and X-10 available from Questar of Charlotte, N.C. and hydrophilic fibers such as Cuprophan available from Enka of Wuppertal, West Germany.

Such chopped hollow fibers or bundles of hollow fibers are then added to a suitable medium for growth of cells and the medium is incubated. Very high cell densities have been observed in the chopped fibers.

This is quite advantageous compared to the traditional methods. Uncontrolled cell growth, leading to membrane damage or disruption is of no consequence. A corollary suggests that defective fibers can be used for immobilization. In hollow fiber bioreactors, continuous lengths of hydrophobic hollow fibers may be used for dispersion-free oxygen supply, carbon dioxide removal, and product extraction uncoupled from the requirement (e.g., hydrophilicity or wetting of hydrophobic fibers) of cell immobilization. The chopped hollow fibers with immobilized cells are almost neutrally buoyant when wetted hydrophobic polypropylene fibers are used. Further, they do not impose any pH limitations encountered in gel entrapment processes. Additionally such fibers, quite often biodegradable, do not pose the waste disposal problems presented by materials such as diatomaceous earth particles and if necessary can be recycled after sterilization.

Although initial experiments with this invention have used a conventional tubular fermentator, a major application of chopped hollow fiber cell immobilization is in bioreactors having continuous lengths of hollow fibers for gas supply and removal as well as insitu product extraction by dispersion-free solvent extraction. Thus, the advantages of matrix entrapment could be grafted independently to the strengths of hollow fiber based bioreactors.

BRIEF DESCRIPTION OF THE DRAWINGS

These and other objects, features and advantages of the present invention will be more readily apparent from the following detailed description of a preferred embodiment of the invention in which.

DETAILED DESCRIPTION OF THE INVENTION

Figure 1:
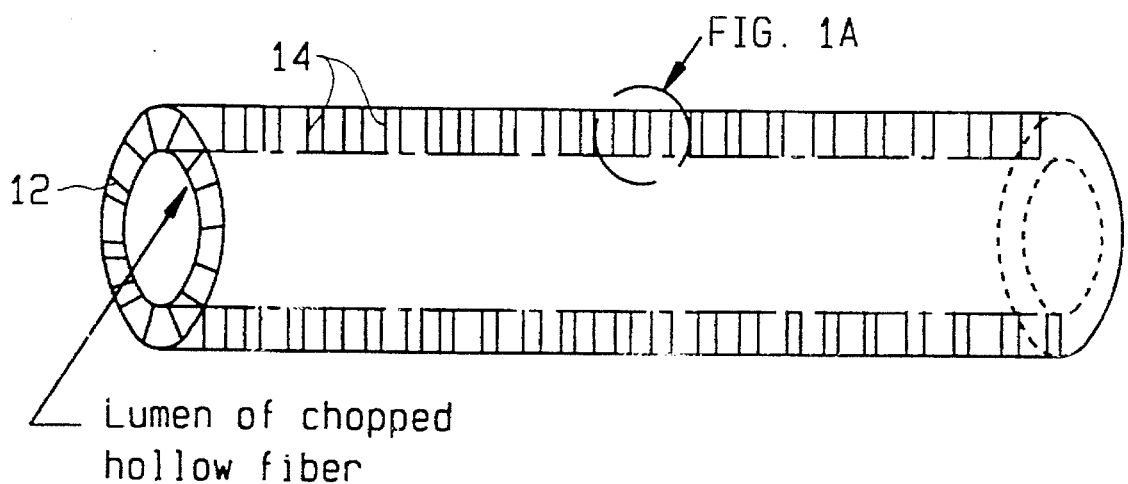
FIG. 1 depicts a chopped hollow fiber illustrative of a preferred embodiment of our invention.

FIG. 1 depicts an illustrative embodiment of a chopped hollow fiber of our invention. As shown, the fiber 10 is a tubular structure having an annular wall 12 through which there are many tiny pores 14. Illustratively the fiber is made of either a hydrophilic material such as cellulose or a hydrophobic material such as polypropylene. Fibers having a hydrophobic outside and a hydrophilic lumen or vice versa may also be used. Fibers of these materials and many others are commercially available. Hydrophobic materials, however, have to be wetted.

Figure 1A:
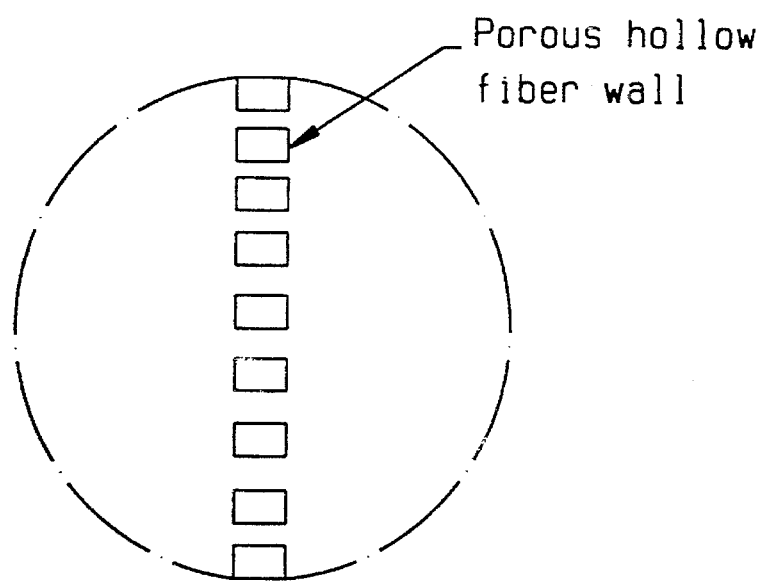
FIG. 1A depicts an expanded view of a wall of the chopped hollow fiber depicted in FIG. 1.

In FIG. 1A, the hollow fiber wall is expanded to depict that the wall is porous.

Figure 9:
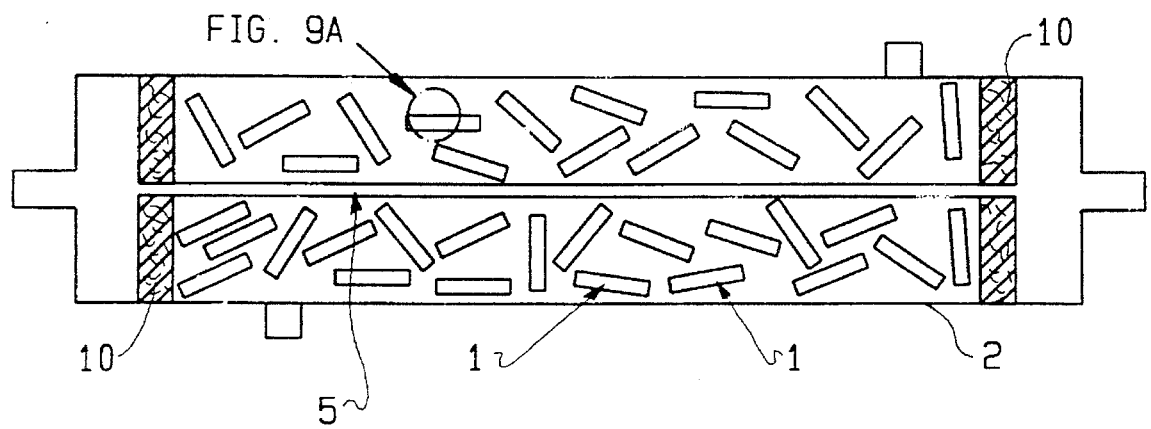
FIG. 9 depicts the bioreactor of the present invention.

The bioreactor of the present invention is illustrated in FIG. 9. Chopped hollow fibers 1, located in fluid container 2 provide for immobilization of whole cells on the chopped hollow fiber surface 3 and lumen 4. At least one continuous length of hollow fiber 5, potted in tube sheets 10, is in communication with the interior 6 of fluid container 2 for gas supply and gas removal and product removal by solvent extraction.

Figure 9A:
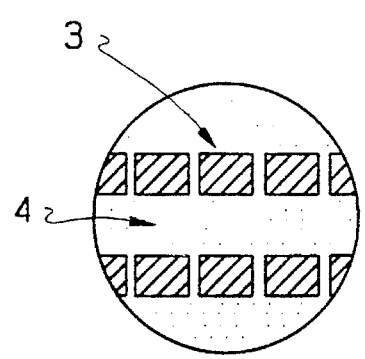
FIG. 9A depicts an expanded view of a chopped hollow fiber of the bioreactor depicted in FIG. 9.

In FIG. 9A, a chopped hollow fiber of the bioreactor of FIG. 9 is expanded to depict that the fiber is hollow and the walls are porous.

Illustrative ranges of pore sizes are from 30 Angstroms to 1 millimeter. The length of the fibers used in the practice of our invention range from about two inches (5 cm.) to about 1/32 inch (0.079 cm) with the shorter lengths being preferred. The interior diameter of the fiber (i.e., the lumen) illustratively is from 5 millimeters to 10 micrometers.

In the practice of the invention, the chopped fibers are prepared by cutting up commercially available lengths of hollow fiber into the lengths desired. If hydrophobic fibers are used, these are then wetted because our experiments reveal that unwetted hydrophobic fibers do not support cell growth. The fibers are then transferred to containers of mediums such as laboratory flasks or fermenters; and the medium is then incubated to grow cells.

EXAMPLES

The invention has been practiced in several experiments using yeast cells and both hydrophobic and hydrophilic microporous hollow fibers. Details of the yeast cells, the fibers and the wetting process for the hydrophobic fibers, which are the same in all examples, are as follows.

Microorganism:

The yeast used was Saccharomyces cerevisiae (NRRL Y-132) supplied by Northern Regional Research Laboratories (Peoria, Ill.). The composition of medium was the same as that given by M. A. Gencer et al. *Biotechnol. Bioeng.* 25: 2243 (1983) which is incorporated herein by reference. The medium was autoclaved before use for fermentation. Inoculum level was about 3% of total volume.

Materials:

Hydrophobic microporous hollow fibers (Celgard X-20 and X-10) were obtained from Questar, Charlotte, N.C. Cuprophan microporous hollow fibers which are hydrophilic, were procured from Enka in Wuppertal, West Germany. The physical characteristics of these fibers are given in Table 1.

TABLE 1

| Membrane | Material | Pore size μm | O.D. μm | I.D. μm | Porosity |
|---|---|---|---|---|---|
| Celgard X-10 | Polypropylene Hydrophobic | 0.03 | 150 | 100 | 0.2 |
| Celgard X-20 | Polypropylene Hydrophobic | 0.03 | 290 | 240 | 0.4 |
| Cuprophan | Regenerated Cellulose | 0.004 (est.) | 200 | 140 | 0.55 |

TABLE 1-continued

| Membrane | Material | Pore size μm | O.D. μm | I.D. μm | Porosity |
|---|---|---|---|---|---|
| | Hydrophilic | | | | |

Wetting Procedure:

The procedure adopted for wetting the hydrophobic Celgard hollow fibers is similar to that described by R. R. Bhave et al *ACS Symp. Ser,* 347: 138 (1987) which is incorporated herein by reference. This technique is based upon wetting the membranes first with a 60% ethanol solution and then replacing the ethanol slowly by sterile water in an exchange process.

Example 1

Fibers of 0.25, 0.5, 1, 1.5, and 2 in. length were prepared by chopping Celgard X-10 and X-20 fibers and Cuprophan fibers to the required lengths. The Celgard fibers were then wetted. The total lengths of fibers used was always kept constant at 192 in. The hollow fibers were weighed before putting them in the medium.

One hundred mL of medium was transferred into each of three 250 mL flasks which had been previously sterilized. The wetted Celgard X-10, X-20 hollow fibers and Cuprophan fibers were then transferred into these flasks. The flasks were kept in an incubator at 30° C. for 120 h. After cell growth, the fibers were withdrawn, washed, and dried overnight in the incubator at 60° C. The weight of hollow fibers was determined and the initial weight of fibers before fermentation was subtracted. The difference in weight of the fibers provided the amount of cells entrapped in the fibers. Alternatively, the cells were taken out from chopped hollow fibers by stirring these fibers in ethanol overnight. The cells were resuspended and centrifuged, washed, and dried. The same procedure was repeated for every fiber length and type.

Table 2 sets forth the measured percentage of dry weight of cells in the fibers to total weight of cells and fibers. These fibers were all wetted; there was no growth on non-wetted fibers.

TABLE 2

| | Type of fibers | | |
|---|---|---|---|
| Length of fibers (in.) | Celgard X-10 | Celgard X-20 | Cuprophan |
| 2.0 | 23.00 | 19.00 | 10.71 |
| 1.5 | 25.00 | 23.53 | 11.63 |
| 1.0 | 28.00 | 25.95 | 13.02 |
| 0.5 | 31.23 | 31.39 | 14.72 |
| 0.25 | 63.30 | 57.10 | 20.00 |

It is clear from the data shown in Table 2 that cell growth depends on the length of fibers. Obviously, 0.25 in. fiber length appears to be highly useful.

The dependence of cell growth on length of chopped fiber suggests considerable resistance to substrate diffusion to the inside of fiber lumen. The cells grow from the ends of fiber lumen to the fiber lumen interior. As the growth proceeds, the ends are blocked by the cells and the substrate and nutrients apparently are not able to diffuse far down the fiber lumen.

We further note that, the cell growth is less in Cuprophan fibers. Cuprophan fibers have a density much higher than that of the medium unlike the Celgard fibers. Because they settle to the bottom more often, part of the surface as well as ends may not be available for cell growth. In addition, the pore size in Cuprophan is much smaller indicating higher resistance to nutrient and substrate transport through the wall pores.

Bundled fibers of Celgard X-20 were also used for cell growth. Each bundle contained 100 fibers in 1 in. length and was tied at the middle. After growth, extraction of cells and weighing, it was found that dried cell amount was 26.34% of the total fibers and cell weight, which is quite close to that for loose fibers. This supports the observation that growth is mainly from the ends of fibers to the interior of fiber lumen.

Example 2

Figure 2:
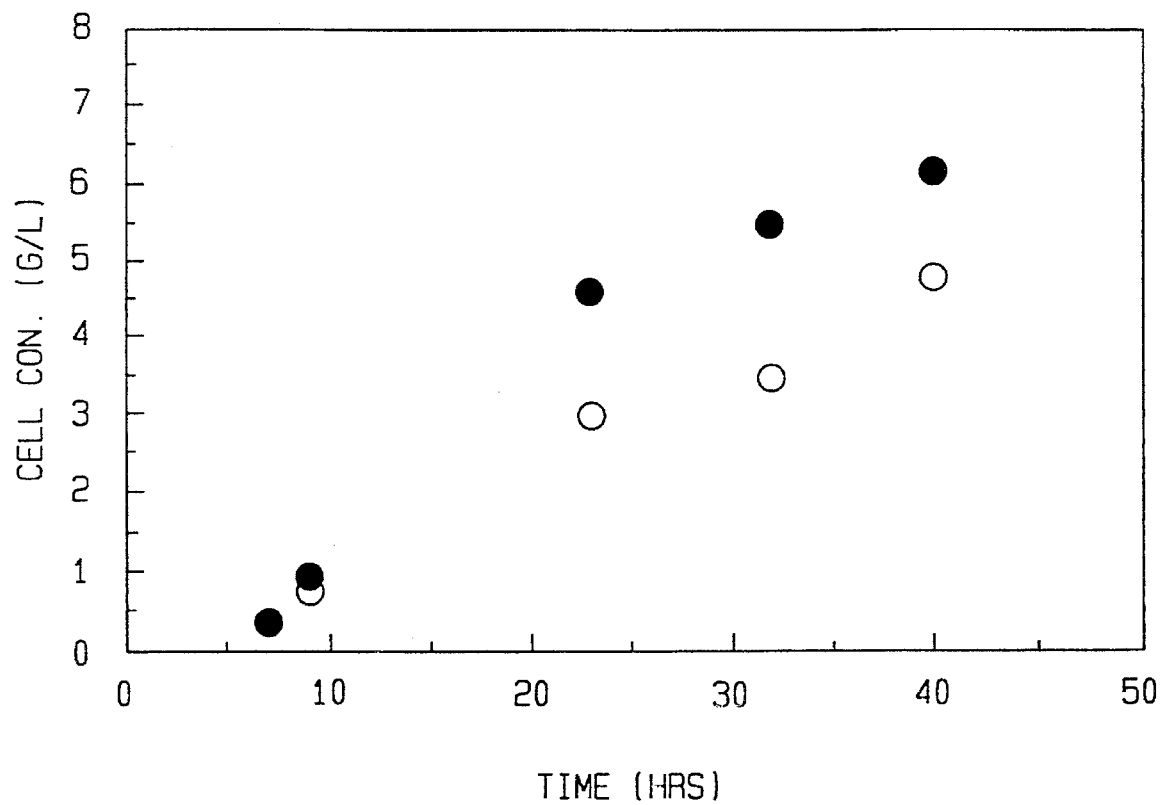
FIG. 2 is a plot of cell concentration versus time for fibers of two different lengths.

The length dependency of cell growth was further confirmed by growing the cells in 1/16" and 1/4" long chopped Celgard hollow fibers in batch culture. These were hydrophobic fibers and the same experimental procedure was followed including wetting. After cell growth, the fibers were taken out and were treated ultrasonically to remove the cells. We were able to remove all the cells as confirmed by a scanning electron microscope photograph of the fiber. The data on the length dependency of Celgard X-20 (400 μm I.D.) fibers are shown in FIG. 2. Here cell concentration per unit of total fiber volume is plotted against time for the two different chopped fiber lengths. Cell growth variation with length is quite clear. It shows that diffusional resistance along the fiber length to the supply of substrate and nutrients from the medium at the two ends of the chopped fiber is crucial to cell growth in fiber lumen.

Example 3

Figure 3:
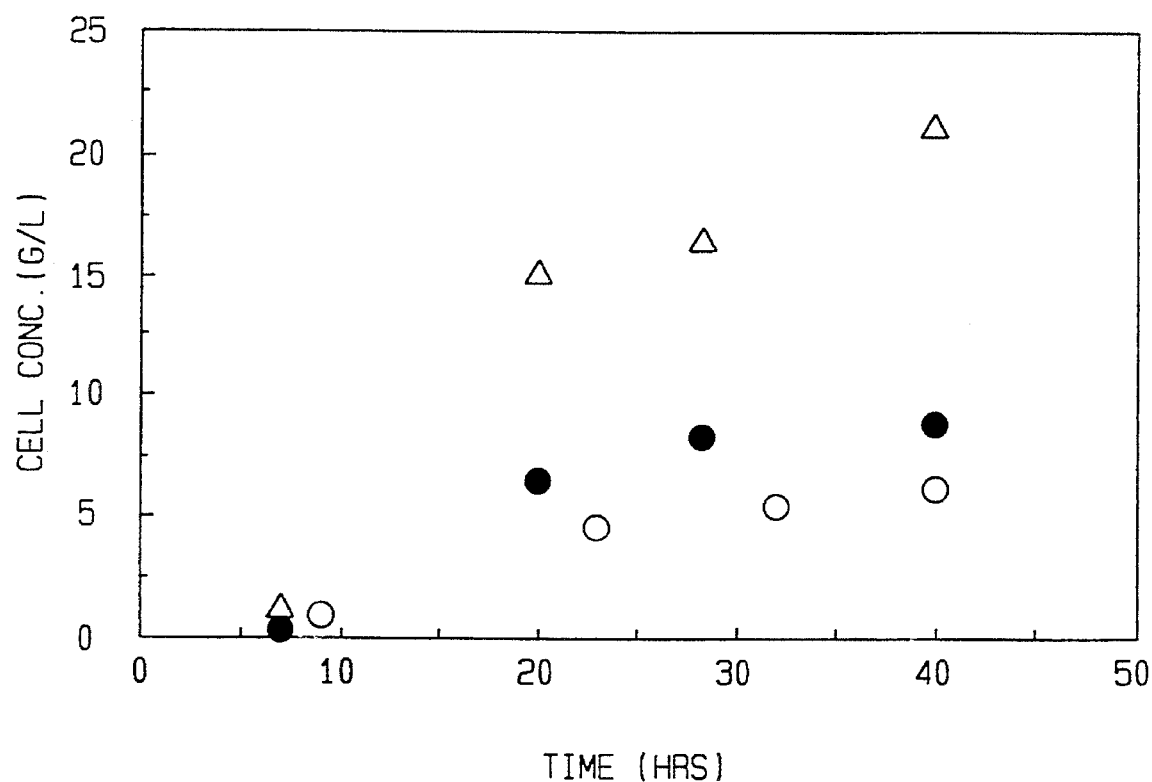
FIG. 3 is a plot of cell concentration versus time for fibers of three different inside diameters.

The effect of the inside diameter dimension of fibers on cell growth was similarly studied. Celgard fibers having different diameters were used. The results are shown in FIG. 3. The cell concentration is based on unit total fiber volume. In fibers with smaller internal diameter, cell growth is considerably higher due most likely to the availability of higher surface area of attachment per unit volume.

Example 4

A conventional tubular fermentor (1.5 ft long packed length and 0.5 inch in diameter) was used to carry out fermentation using chopped hollow fibers as immobilization support. The tubular fermentor had five sampling ports. Yeast cells were grown in chopped hydrophilic hollow fibers (Cuprophan, 0.125 inch in length, total weight 10.17 gm) in shaker flasks. Then the whole spent broth containing the chopped fibers was poured in tubular fermentor. A wire mesh (about 40 mesh) was used at both ends of the fermentor to retain the fibers while the spent broth was drained. Fresh medium was then passed through the fermentor to carry out fermentation; and spent medium was collected in another vessel. A constant pressure nitrogen cylinder was used to pump the medium at a controlled rate. Samples were collected at different time intervals for analysis. Experiments were carried out for a total time of 240 hours. Variations in flow and inlet glucose concentrations were introduced at steady state.

Figure 4:
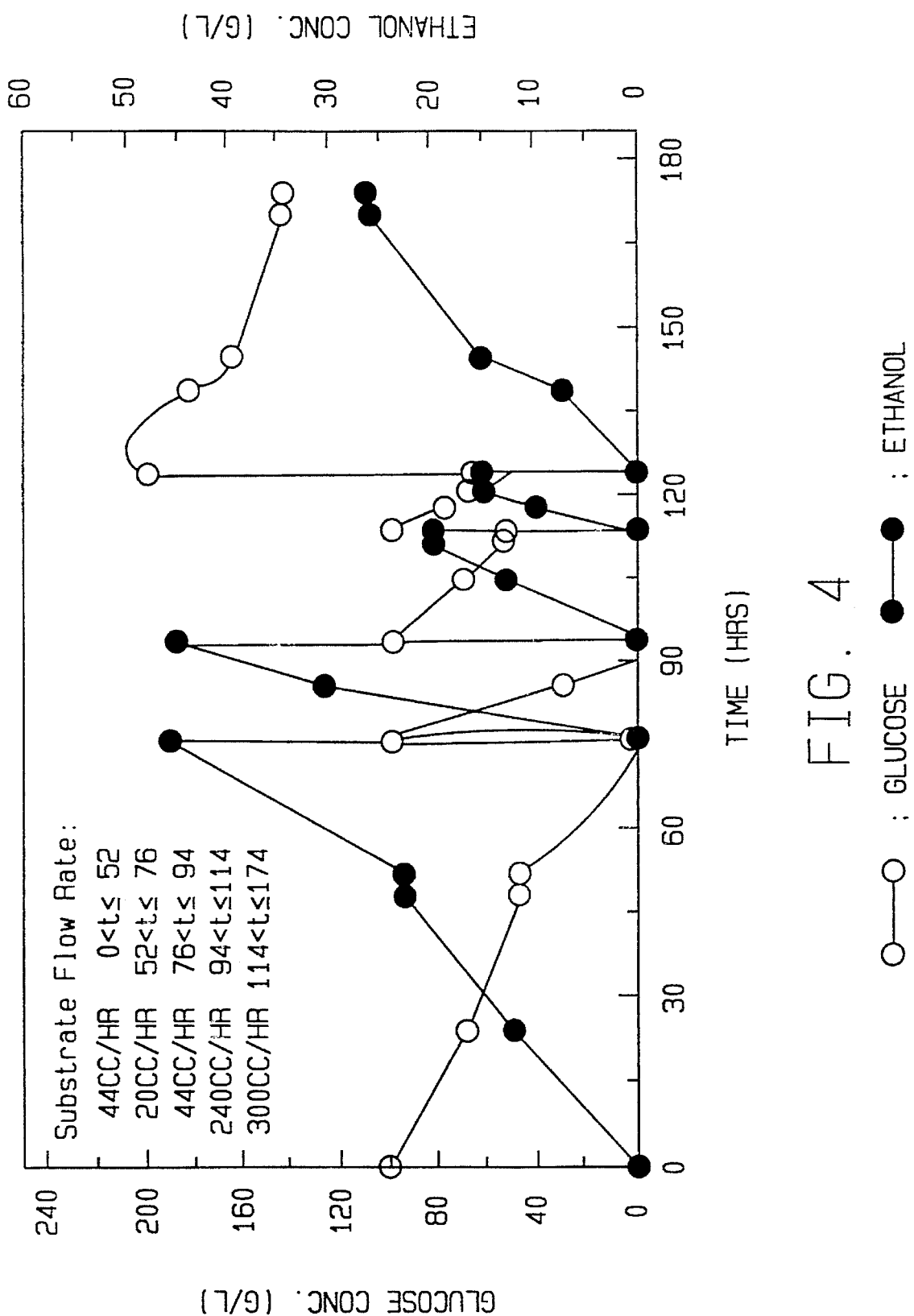
FIG. 4 is a plot of concentration of glucose and ethanol in a fermentor as a function of time.
Figure 5:
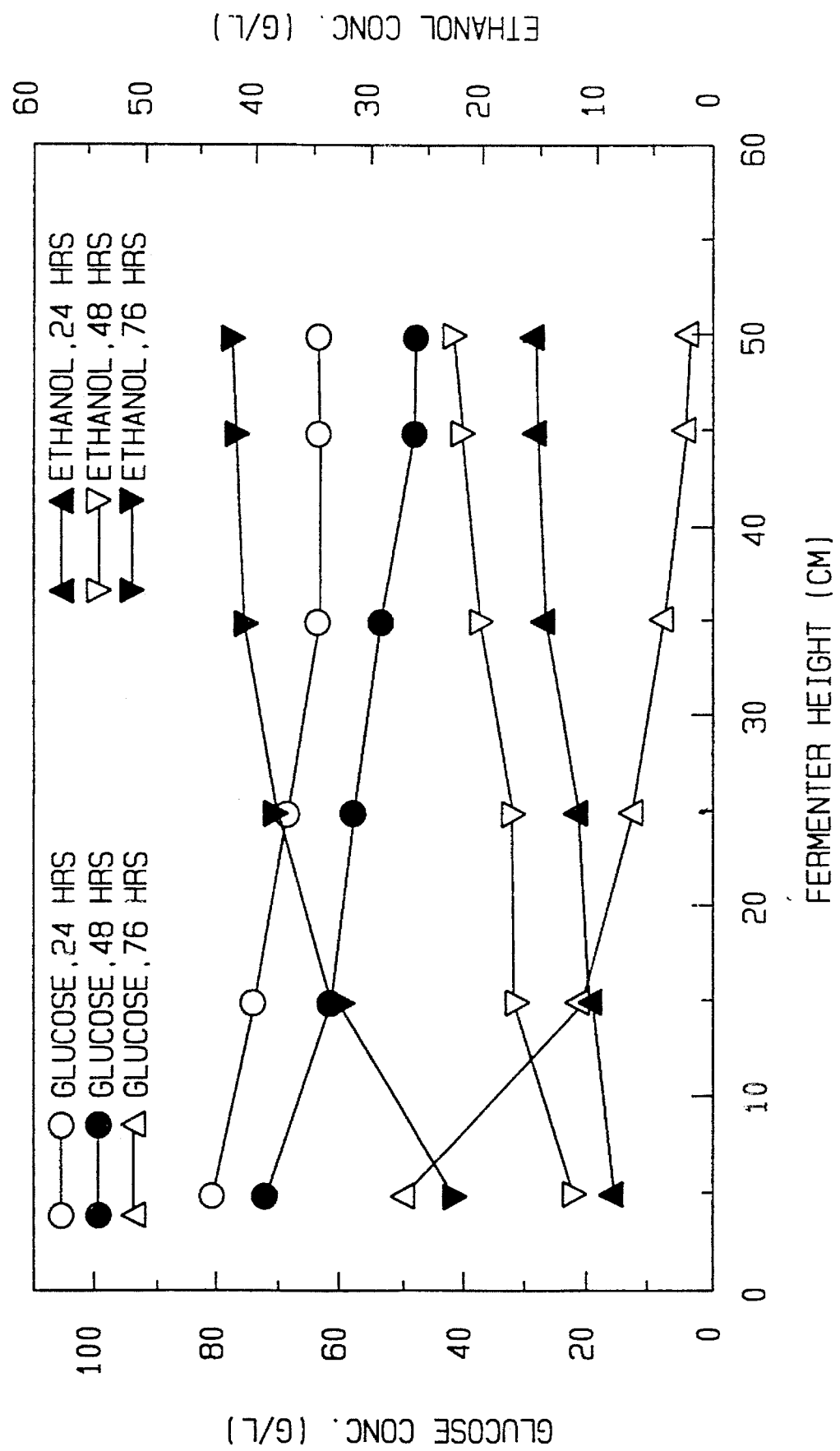
FIG. 5 is a plot of concentration of glucose and ethanol as a function of fermentor height.

The results are shown in FIG. 4. The substrate flow rate as well as the initial glucose concentration were varied. It can be observed that glucose and ethanol concentrations reach steady values for a feed glucose concentration of 200 g/l; however, all glucose is consumed for a feed glucose concentration of 100 g/l. Concentration profiles of glucose and ethanol along the fermentor length at different times are shown in FIG. 5 for a feed glucose concentration of 100 g/l. It is obvious that fermentation is slow near the end of the fermentor. The productivity of the system is reported in Table 3.

TABLE 3

| Feed Glucose Concentration, g/l | Flow Rate ml/hr | Ethanol Productivity g/l-hr |
| --- | --- | --- |
| 100 | 44 | 28.9 |
| 100 | 240 | 67.3 |
| 100 | 300 | 65.0 |
| 200 | 300 | 107.8 |

A very high ethanol productivity of 107.8 g/l-hr is obtained. This compares well with some of the best ethanol productivities of 82 and 133 g/l-hr reported in literature.

Figure 6:
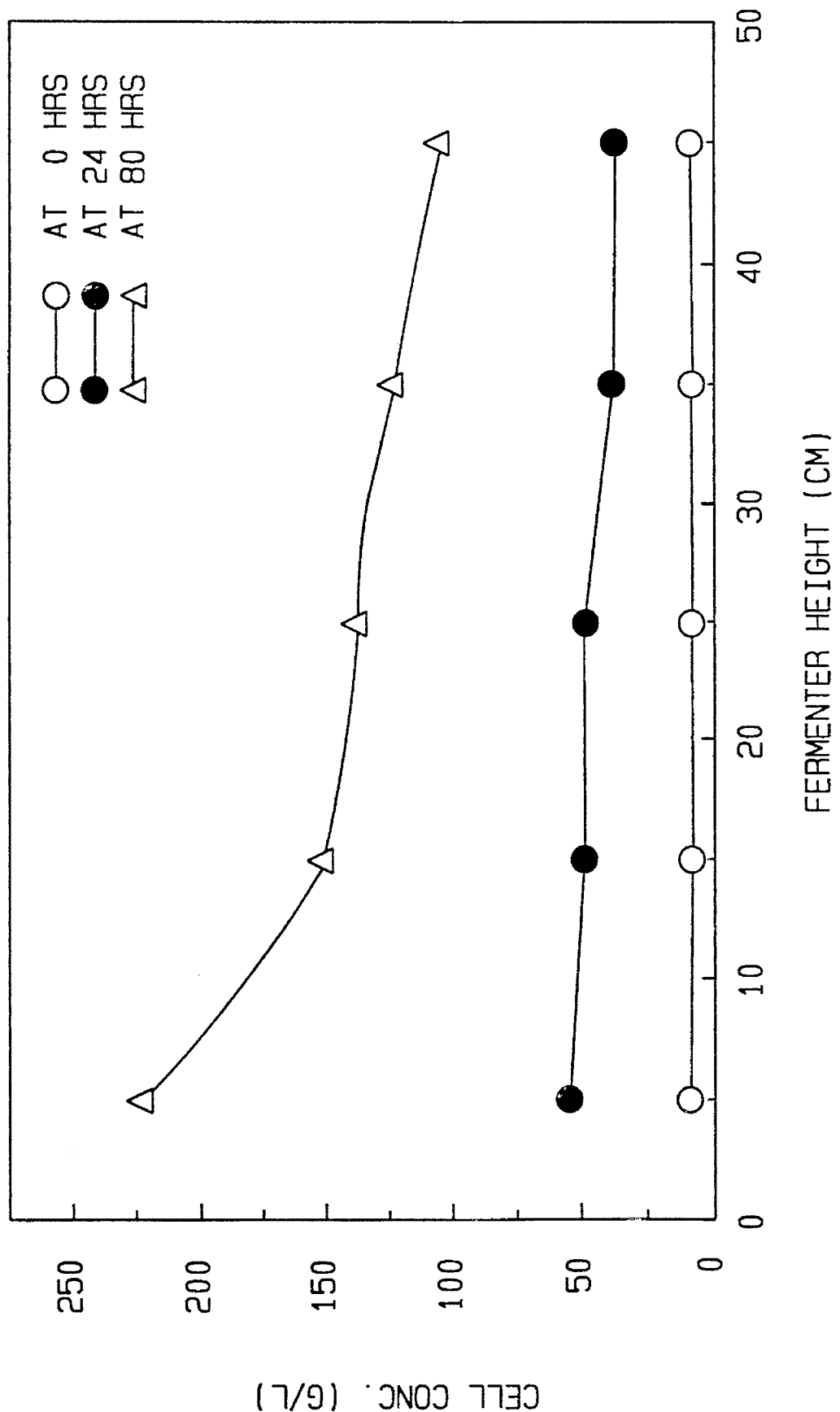
FIG. 6 is a plot of cell concentration at different times as a function of fermentor height.

The cell concentration along the fermentor length in the tubular bioreactor is shown in FIG. 6. The cell density after 24 hrs of fermentation is almost independent of the fermentor length since cells were grown in these fibers outside in batch mode. With an increase in time, the cell growth near the fermentor inlet is much higher than that at exit. This is due to the availability of less glucose at fermentor exit. However, the extent of cell growth at the exit is still considerable.

A maximum cell concentration of $9.2 \times 10^9$ cells per unit fiber lumen volume ($4.5 \times 10^9$ cells per unit of fiber volume) is obtained near the fermentor entrance at 80 hrs. This value is quite high. Similar results were obtained in other studies.

Example 5

We have also carried out ethanol fermentation in a tubular bioreactor with wetted chopped Celgard X-20 hollow fibers (0.25 in. long) for ethanol production using Saccharomyces cerevisiae. Chopped hollow fibers (Celgard X-20) of 1/4 in. length were filled in a tubular fermentor (length 1.5 ft., I.D. 1 in.) having a total volume of 94.6 mL and void volume of 73 mL. The total weight of chopped hollow fiber in the fermentor was 3.804 g. Ethanol (50% v/v), was introduced in the fermentor to wet the fibers, and kept for four hours. Sterile water was then passed continuously to replace ethanol. After wetting, the medium was introduced into the fermentor and the fermentor was then inoculated with previously grown cells. The cells were allowed to grow for two days. After growth, the broth was drained and regular medium was allowed to flow.

Figure 7:
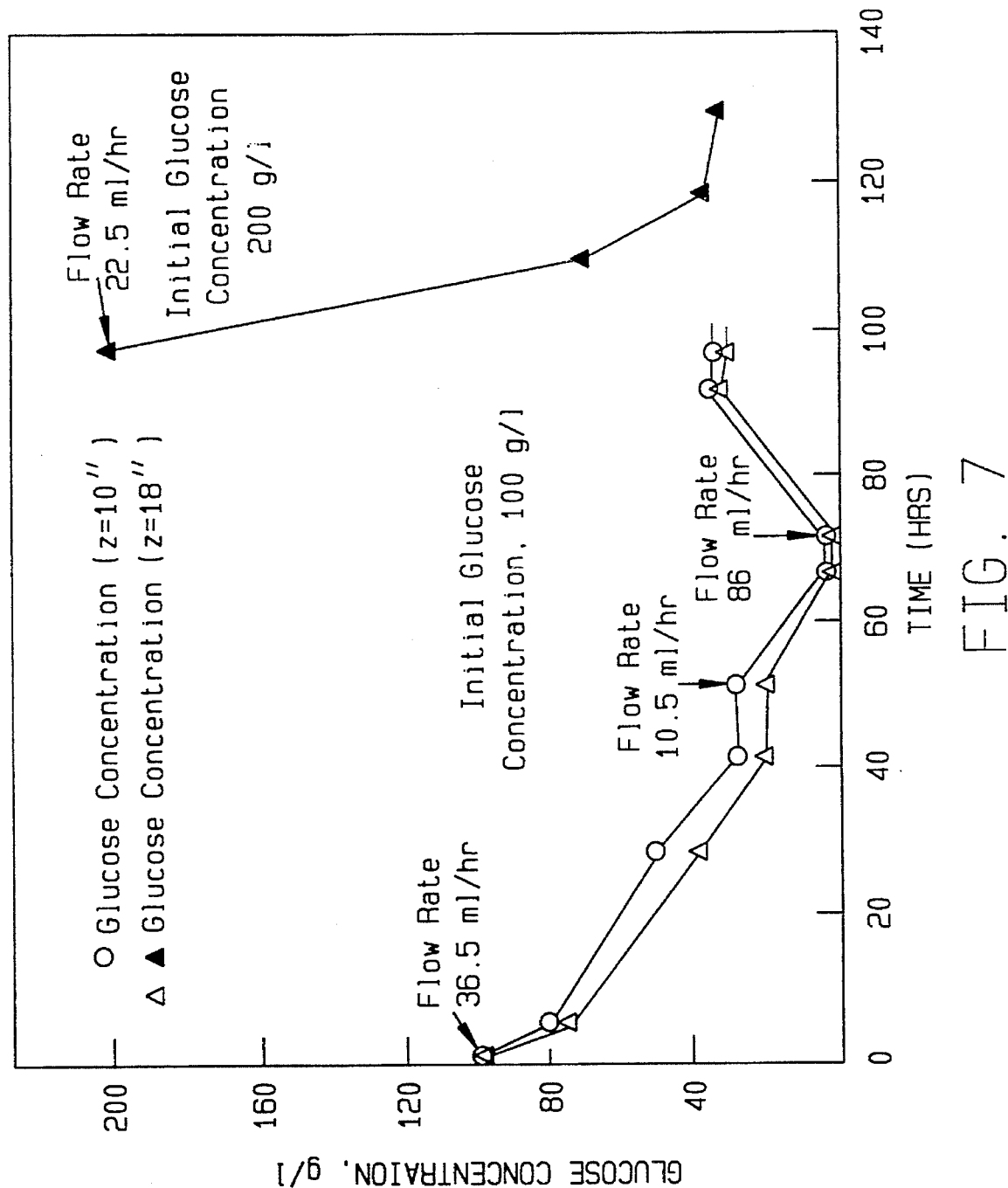
FIG. 7 is a plot of glucose concentration versus time.
Figure 8:
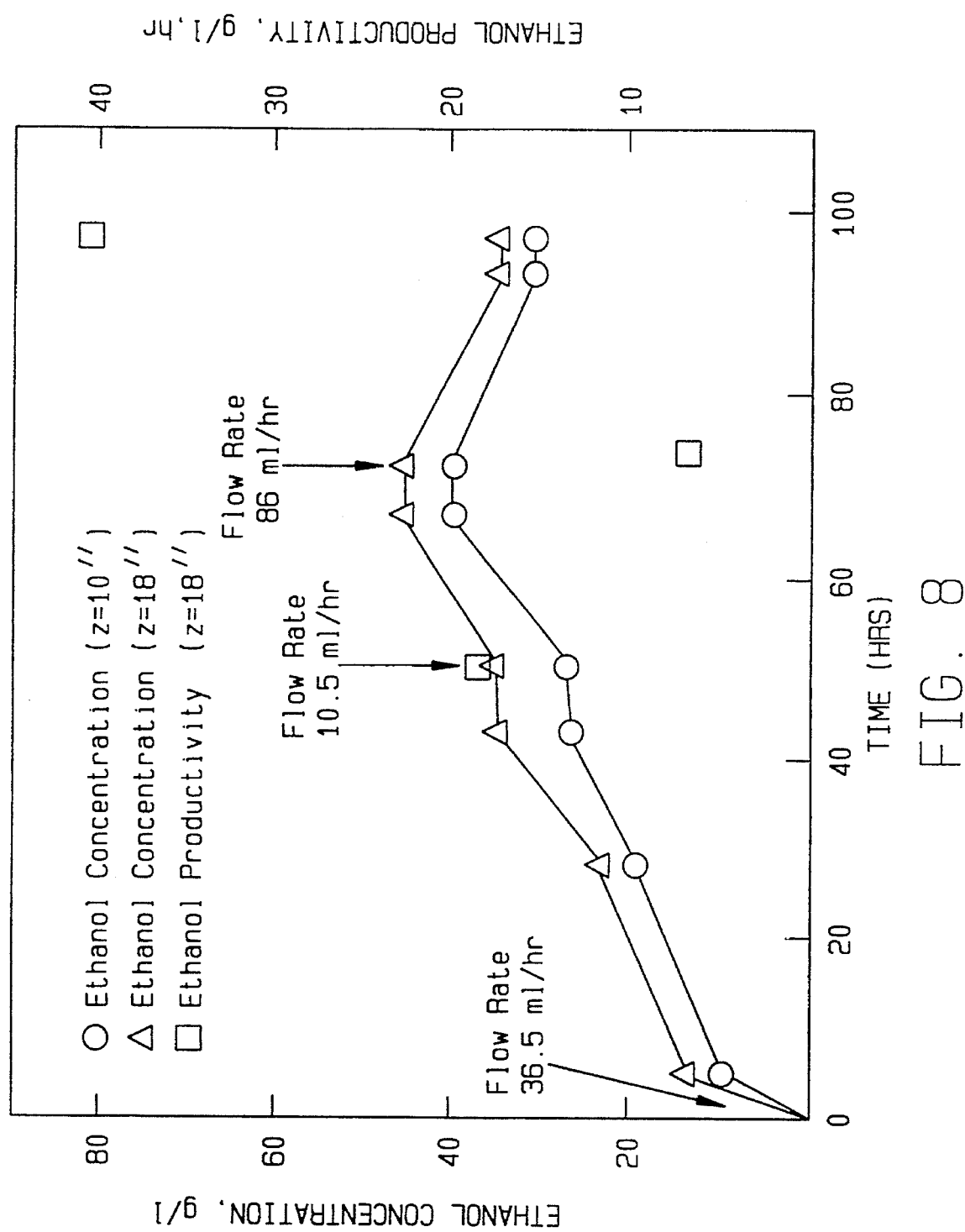
FIG. 8 is a plot of ethanol concentration and ethanol productivity versus time.

The glucose concentration remaining in the waste substrate exiting the reactor has been plotted against time at different flowrates as well as at two values of initial glucose concentrations in FIG. 7. We can see that the total amount of glucose is consumed quickly when initial glucose concentration was 100 g/L, whereas it is not true with an initial concentration of 200 g/L. In the latter case, the glucose consumption stops when residual concentration reaches about 34 g/L. This indicates that ethanol concentration has reached the toxicity level. The ethanol concentration and ethanol productivity are shown in FIG. 8. An ethanol concentration of 45 g/L and an ethanol productivity of 41 g/L-h are obtained at an initial glucose concentration of 100 g/L. The ethanol productivity can be increased further without much difficulty.

As will be apparent to those skilled in the art, numerous modifications may be made within the spirit and scope of the invention. While the invention has been described in terms of the immobilization of yeast cells, the invention may be practical on any type of microbial cells well as plant and animal cells. While the invention has been described in terms of cellulose and polypropylene fibers, it will be understood it can be practiced with any type of hydrophobic or hydrophilic fiber as well as with fibers which are hydrophobic on one side and hydrophilic on the other. It may also be practiced with other types of fibers such as ion exchange hollow fibers with positively or negatively charged surface. The optimum length of hollow fiber to be used in the practice of the invention depends on the particular cell that is immobilized by the fiber. From the procedures detailed above, determination of suitable lengths can be made experimentally.

In addition to the advantages of chopped hollow-fibers in fostering cell growth, the fibers are also useful in transportation of cells. In particular, we have found that the cells can be sealed into the fibers simply by epoxying the ends of the fibers and fibers that are so sealed can readily be moved without loss of cells.

What is claimed is:

1. An immobilization support for whole cells comprising a chopped microporous hollow fiber having a length between 0.6 centimeters and 5.0 centimeters.

2. The support of claim 1 wherein the microporous hollow fiber is hydrophobic and the fiber has been wetted.

3. An immobilization support for whole cells comprising a chopped microporous hollow fiber having a length of five centimeters or less wherein the exterior surface of the microporous hollow fiber is hydrophobic and the inside surface of the microporous hollow fiber is hydrophilic.

4. An immobilization support for whole cells comprising a chopped microporous hollow fiber having a length of five centimeters or less wherein the exterior surface of the microporous hollow fiber is hydrophilic and the inside surface of the microporous hollow fiber is hydrophobic.

5. A bioreactor comprising:

a fluid container;

means including at least one continuous length of hydrophobic hollow fiber having ends potted in tube sheets for gas supply and removal and product removal by solvent extraction; and a plurality of chopped microporous hollow fibers having lengths of five centimeters or less, said chopped hollow fibers being located in said container and providing for immobilization of whole cells on a lumen and exterior of said chopped hollow fibers;

wherein the chopped hollow fibers are hydrophobic and the fibers have been wetted.

6. A bioreactor comprising:

a fluid container;

means including at least one continuous length of hydrophobic hollow fiber having ends potted in tube sheets for gas supply and removal and product removal by solvent extraction; and a plurality of chopped microporous hollow fibers having lengths of five centimeters or less, said chopped hollow fibers being located in said container and providing for immobilization of whole cells on a lumen and exterior of said chopped hollow fibers;

wherein the exterior surfaces of the plurality of chopped microporous hollow fibers are hydrophobic and the inside surfaces of the plurality of chopped microporous hollow fibers are hydrophilic.

7. A bioreactor comprising:

a fluid container;

means including at least one continuous length of hydrophobic hollow fiber having ends potted in tube sheets for gas supply and removal and product removal by solvent extraction; and a plurality of chopped microporous hollow fibers having lengths of five centimeters or less, said chopped hollow fibers being located in said container and providing for immobilization of whole cells on a lumen and exterior of said chopped hollow fibers;

wherein the exterior surfaces of the plurality of chopped microporous hollow fibers are hydrophilic and the inside surfaces of the plurality of chopped microporous hollow fibers are hydrophobic.

8. A bioreactor comprising:

a fluid container;

means including at least one continuous length of hydrophobic hollow fiber having ends potted in tube sheets for gas supply and removal and product removal by solvent extraction; and a plurality of chopped microporous hollow fibers having lengths of five centimeters or less, said chopped hollow fibers being located in said container and providing for immobilization of whole cells on a lumen and exterior of said chopped hollow fibers;

wherein the continuous length of hydrophobic hollow fiber is microporous.

9. A method of immobilizing whole cells comprising the steps of:

chopping microporous hollow fibers into short sections of fibers having a length of approximately five centimeters or less;

combining said sections of fibers with a medium suitable for growth of whole cells; and growing whole cells on the inside surfaces and on the exterior surfaces of said sections of fibers by incubating said medium;

wherein the plurality of chopped microporous hollow fibers are hydrophobic and the fibers have been wetted.

10. The method of claim 9 wherein the whole cells are selected from the group consisting of microbial, plant and animal cells.

11. A method of immobilizing whole cells comprising the steps of:

chopping microporous hollow fibers into short sections of fibers having a length of approximately five centimeters or less;

combining said sections of fibers with a medium suitable for growth of whole cells; and growing whole cells on the inside surfaces and on the exterior surfaces of said sections of fibers by incubating said medium;

wherein the exterior surfaces of the plurality of chopped microporous hollow fibers are hydrophilic and the inside surfaces of the plurality of chopped microporous hollow fibers are hydrophobic.

12. The method of claim 11 wherein the whole cells are selected from the group consisting of microbial, plant and animal cells.

13. A method of immobilizing whole cells comprising the steps of:

chopping microporous hollow fibers into short sections of fibers having a length of approximately five centimeters or less;

combining said sections of fibers with a medium suitable for growth of whole cells; and growing whole cells on the inside surfaces and on the exterior surfaces of said sections of fibers by incubating said medium;

wherein the exterior surfaces of the plurality of chopped microporous hollow fibers are hydrophobic and the inside surfaces of the plurality of chopped microporous hollow fibers are hydrophilic.

14. The method of claim 13 wherein the whole cells are selected from the group consisting of microbial, plant and animal cells.

* * * * *